United States Patent [19]
Christy

[11] 3,972,936
[45] Aug. 3, 1976

[54] 10,11-DIHYDRO-5-(3-AMINO-PROPYL-OR-PROPYLIDENE)-10,10,11,11-TETRA-FLUORO-5H-DIBENZO[a,d]CYCLOHEPTENES AND-5-OLS

[75] Inventor: Marcia Elizabeth Christy, Perkasie, Pa.

[73] Assignee: Merck & Co., Inc., Rahway, N.J.

[22] Filed: Feb. 1, 1974

[21] Appl. No.: 438,923

[52] U.S. Cl. ............... 260/570.8 TC; 260/240 TC; 260/243 R; 260/247.7 Z; 260/293.56; 260/471 C; 260/501.1; 260/556 AR; 260/556 C; 260/590 FB; 260/607 A; 260/609 R; 260/611 F; 260/612 R; 260/618 D; 260/618 F; 260/649 F; 424/316; 424/330
[51] Int. Cl.² .................. C07C 87/28; C07C 87/29
[58] Field of Search ............... 260/570.8 TC, 501.1

[56] References Cited
UNITED STATES PATENTS 3,445,519  5/1969  Kallonitoch.................... 260/570.8
3,574,199  4/1971  Coyne et al................. 260/570.8 X Primary Examiner—Robert V. Hines
Attorney, Agent, or Firm—Harry E. Westlake, Jr.; Thomas E. Arther; William H. Nicholson

[57] ABSTRACT

Tetrafluoro derivatives of 10,11-dihydro-5H-dibenzo[a,d]cycloheptene-5-propylamine and 10,11-dihydro-5H-dibenzo[a,d]cycloheptene-Δ-5-γ-propylamine, useful as antidepressants, are prepared from the known 10,11-dihydro-5H-dibenzo[a,d]cycloheptene-10,11-dione by fluorination at the 10,11-position using sulfur tetrafluoride followed by introduction of the amino propylidine or the amino propyl substituent at the 5- position by reaction of the 5-keto or 5-halo-10,10,11,11-tetrafluoro derivative with the appropriate Grignard reagent.

10 Claims, No Drawings

10,11-DIHYDRO-5-(3-AMINO-PROPYL-OR-PROPYLIDENE)-10,10,11,11-TETRA-FLUORO-5H-DIBENZO[a,d]CYCLOHEPTENES AND-5-OLS

This invention relates to tetrafluoro derivatives of 10,11-dihydro-5H-dibenzo[a,d]cycloheptene-5-propylamine and tetrafluoro derivatives of 10,11-dihydro-5H-dibenzo[a,d]-cycloheptene-Δ-5-γ-propylamines and the corresponding N-substituted derivatives, such as the N-alkyl and the N,N-dialkyl derivatives thereof, which are useful in the treatment of depression.

BACKGROUND OF THE INVENTION

The treatment of mental depression accompanied by anxiety has been assisted in the past by administration of a variety of hetero and homo tricyclic compounds having aliphatic amino, particularly aminopropyl and aminopropylidene, substituents attached to the central ring of the tricyclic compound. Active compounds discovered to be useful in this method of treatment include the heterocyclic compounds imipramine and desipramine and the homocyclic compounds amitriptyline, nortriptyline and protriptyline. These compounds differ widely in their potencies and in the types of pharmacological properties. However, it is well known through metabolic studies that these compounds, depicted below, are subject to oxidation of the central ring structure at the 10- or 11- carbons, i.e., the ethane or ethylene bridge between the two benzene rings:

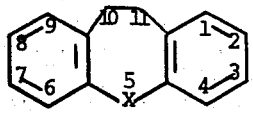

wherein

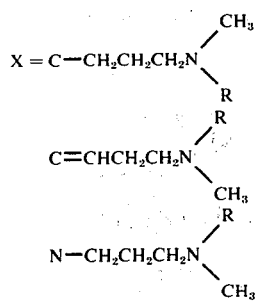

in which R is H or $CH_3$.

In accordance with the present invention, there is produced a class of 10,11-dihydro-5H-dibenzo[a,d]cycloheptene compounds which have a perfluorinated ethane substituent bridging the benzene rings. This perfluoroethyl bridge is resistant to known chemical means of oxidation. This class of compounds, however, is active as antidepressants, as shown by their ability to combat the sedative effects of the reserpine derivative, tetrabenazine, in an animal model of depression. These compounds are useful in the treatment of humans affected by mental depression accompanied by anxiety and agitation, since these compounds possess tranquilizing activity in addition to their antidepressant effect. Many of the compounds presently used in treating depression have a strong excitatory or stimulatory effect on the central nervous system which can lead to undesirable anxiety and agitation in the patient being treated. In animal tests conducted on the compounds of the present invention, no strong stimulatory effect was noted.

The compounds of the present invention are depicted in the following structural formula:

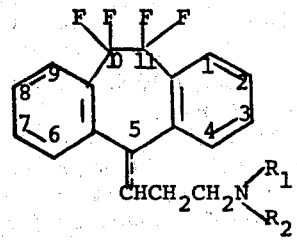

in which
$R_1$ and $R_2$ can be alike or different and are either hydrogen, alkyl, aralkyl, alkenyl, alkynyl, or can be joined together through an atom of nitrogen, oxygen or sulfur to form a heterocyclic ring of from 5–6 atoms, or a derivative thereof in which one or more of the hydrogen atoms attached to the 1-, 2-, 3-, 4-, 6-, 7-, 8- or 9- positions is replaced by halogen, alkyl, alkoxy, perfluoroalkyl, alkylmercapto, alkylsulfonyl, and dialkylsulfamoyl.

This invention also relates to the novel processes and the novel intermediates utilized in the production of the new 10,10,11,11-tetrafluoro-5H-dibenzo[a,d]cycloheptene-5-propylamines and the corresponding Δ-5-γ-propylamines, as well as the N-alkyl and the N,N-dialkyl derivative, e.g., the N-methyl or N-ethyl and the N,N-dimethyl or the N,N-diethyl derivatives thereof.

The invention further relates to antidepressant pharmaceutical formulations of the new tetrafluorodibenzo[a,d]cycloheptene-5-propylamines and the corresponding Δ-5-γ-propylamines and to methods of treating mental depression and particularly mental depression accompanied by anxiety or agitation, using the novel compounds and/or pharmaceutical formulations thereof described hereinafter.

A preferred group of compounds included within the scope of the present invention are compounds of the above formula in which the $R_1$ and $R_2$ substituents are preferably loweralkyl substituents of from 1-6 carbon atoms or hydrogen, and one to two of the ring substituent at the 1-, 2-, 3-, 4-, 6-, 7-, 8- or 9- position is either hydrogen, halogen selected from chlorine or fluorine, loweralkyl of from 1-6 carbon atoms, loweralkoxy of from 1-5 carbon atoms, or trifluoromethyl.

An especially preferred group of compounds included within the scope of the present invention is represented by the formula

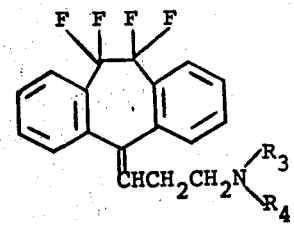

in which $R_3$ and $R_4$ substituents are each either hydrogen or loweralkyl of from 1-6 carbon atoms.

Illustrative of the compounds included within the scope of my invention are 10,11-dihydro-10,10,11,11-tetrafluoro-5H-dibenzo[a,d]cycloheptene-5-propylamine, the N-methyl derivative of 10,11-dihydro-10,10,11,11-tetrafluoro-5H-dibenzo[a,d]cycloheptene-5-propylamine, the N,N-dimethyl derivative of 10,11-dihydro-10,10,11,11-tetrafluoro-5H-dibenzo[a,d]cycloheptene-5-propylamine, 10,11-dihydro-10,10,11,11-tetrafluoro-5H-dibenzo[a,d]-cycloheptene-Δ-5-γ-propylamine, the N-methyl derivative of 10,11-dihydro-10,10,11,11-tetrafluoro-5H-dibenzo[a,d]-cycloheptene-Δ-5-γ-propylamine, and the N,N-dimethyl derivative of 10,11-dihydro-10,10,11,11-tetrafluoro-5H-dibenzo[a,d]cycloheptene-Δ-5-γ-propylamine.

Also included among the compounds useful in the method of the present invention are the N-oxides of the tertiary amines and the non-toxic pharmaceutically acceptable salts of the amines and N-oxides, the preferred salts being the non-toxic acid addition salts such as the hydrochloride, the maleate, and the like.

The compounds represented above in either the free base or salt form possess useful pharmacologic properties. In particular, they have been found to possess antidepressant and tranquillizing activity. It has been found that the administration of the compounds of the present invention depicted in the above formulae counteracts the sedative effects of the reserpine derivative, tetrabenazine, in an animal model of depression. These compounds are therefore useful in the treatment of depression in humans, particularly depression accompanied by anxiety or agitation. As antidepressant drugs, these compounds may be administered either orally or parenterally. The formulations for administration may be prepared in conventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, fumaric acid, acetic acid, propionic acid, lactic acid, gluconic acid, maleic acid, succinic acid, tartaric acid, and the like. Salts of these acids with the amine base are useful as the active components of the compositions in the method of this invention.

Daily doses are based on body weight of the test animal and vary between 1 and 100 mg./kg./day for mature animals. For larger animals, up to 100 kg. and above, proportional doses are employed based on the weight of the animal. For the treatment of depression in humans, therefore, a unit dosage form of from 1–25 mg./dose is satisfactory for administration on a 4-times-a-day schedule. Suitable dosage units provided for the administration of the compositions used in the method of the invention are tablets, capsules (which can be suitable formulated for either immediate or sustained release), syrups, elixirs, parenteral solutions and the like. These dosage forms preferably contain per unit one or more multiples of the desired dosage unit in combination with the pharmaceutically acceptable diluent or carrier required for preparing the dosage unit.

In treating depression in humans with antidepressants it is preferable to first administer a minimal amount of medication and then to increase the dose by one dosage unit per day until an antidepressant effect is noted. Ordinarily, the antidepressant effect is evident within 3 or 4 days but may take as long as 30 days to become evident. It is important to note that individual variation among patients with respect to the total daily dosage as well as with respect to the lag in effect requires individualization of dose to the patient being treated.

The compounds represented by the above structural formulae may be prepared as illustrated below:

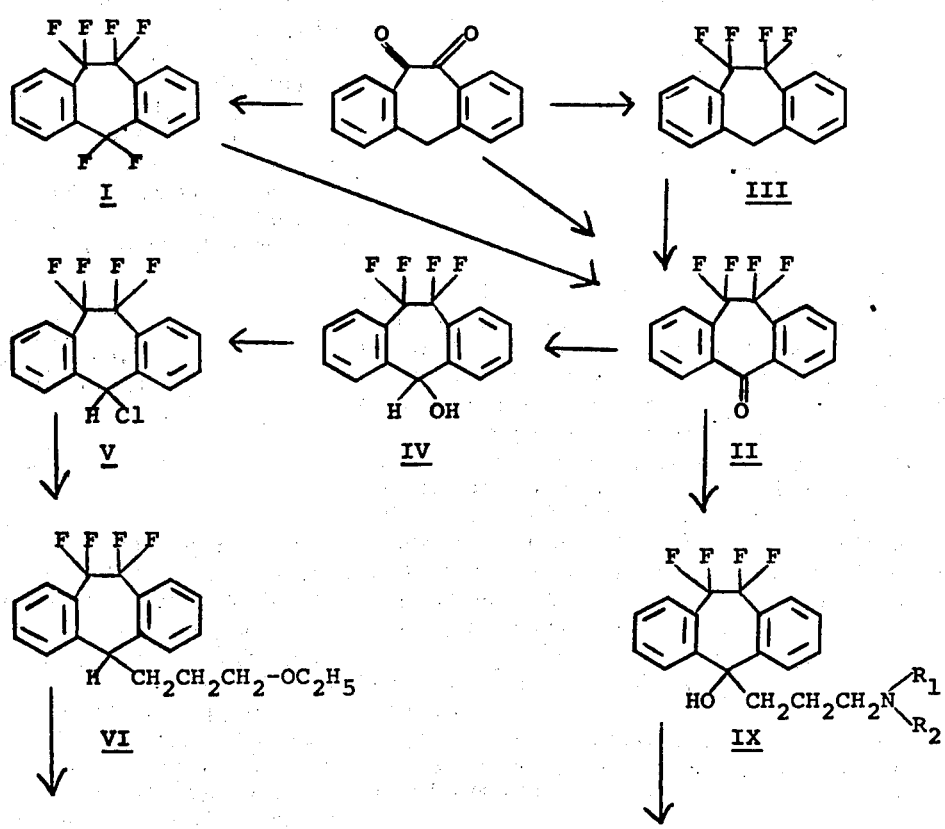

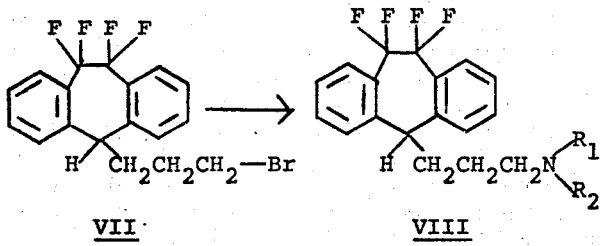
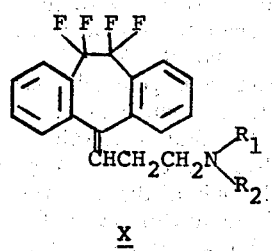

in which

R₁ and R₂ are alike or different and are either hydrogen, alkyl, aralkyl, alkenyl, alkynyl, or can be joined together through an atom of nitrogen, oxygen or sulfur to form a heterocyclic ring of from 5–6 atoms, or a derivative thereof in which one or more of the hydrogen atoms attached to the 1-, 2-, 3-, 4-, 6-, 7- 8- or 9- positions is replaced by halogen, alkyl, alkoxy, perfluoroalkyl, alkylmercapto, alkylsulfonyl, and dialkylsulfamoyl. As indicated above, the aromatic rings of the above compounds are substituted optionally by replacement by one or more of the hydrogen atoms attached to the 1-, 2-, 3-, 4-, 6-, 7-, 8-, or 9- positions by halogen, especially chlorine or bromine, alkyl, preferably of from 1–6 carbon atoms, alkoxy, preferably loweralkoxy of from 1–5 carbon atoms, perfluoroalkyl, especially trifluoromethyl or pentafluoroethyl, alkylmercapto, preferably containing from 1–6 carbon atoms, alkylsulfonyl, preferably of from 1–6 carbon atoms, and dialkylsulfamoyl, preferably having from 2–8 carbon atoms.

In carrying out the process of the above invention, the critical steps are those employed in preparing intermediate ketone II, i.e., the 10,11-dihydro-10,10,11,11-tetrafluoro-5H-dibenzo[a,d]cyclohepten-5-one. In preparing this ketone from the known starting material, 10,11-dihydro-5H-dibenzo[a,d]cycloheptene-10,11-dione by reaction with a large excess of sulfur tetrafluoride in the presence of mercury and a trace of hydrogen fluoride, certain alternate reactions occur which produce fluorinated intermediates which may then be converted to the desired final product.

When the starting 10,11-dione compound is treated with sulfur tetrafluoride in the presence of mercury and hydrogen fluoride at temperatures in excess of 100°C., the desired tetrafluorodibenzocycloheptenone is produced directly; thus, in a preferred method of producing the 10,11-dihydro-10,10,11,11-tetrafluoro-5H-dibenzo[a,d]cyclohepten-5-one it is preferred to first mix the diketone, excess sulfur tetrafluoride, mercury, and a trace of hydrogen fluoride in a sealed vessel generally impervious to the action of hydrogen fluoride, and agitate for a period of from 1–3 hours, preferably 2 hours, at 120°C., then raise the temperature for an additional 2-hour period to 140°C., followed by an additional 6-hour period at 160°C. The same result is accomplished by heating the mixture in an enclosed vessel over a period of 10 hours rapidly at first to 120°C. and then at a slower rate until the temperature reaches 160°C., which is maintained for a period of from 4–10 hours and preferably for about 6 hours. In this manner, the product 10,11-dihydro-10,10,11,11-tetrafluoro-5H-dibenzo[a,d]cyclohepten-5-one is produced directly and may be purified by a combination of extraction, sublimation, and crystallization.

In an alternative method of preparing the desired tetrafluoro ketone, the starting 10,11-dihydro-5H-dibenzo[a,d]-cycloheptene-10,11-dione is converted to Compound I. The 10,11-dihydro-5,5,10,10,11,11-hexafluoro[a,d]cycloheptene is heated for a period of from 8–12 hours, preferably about 10 hours, at 80°C., mixed with excess sulfur tetrafluoride, mercury, and a trace amount of hydrogen fluoride. The product produced in this manner may be isolated by extraction, sublimation, and chromatography on silica gel. The product produced in this manner is then converted to the desired 10,11-dihydro-10,10,11,11-tetrafluoro-5H-dibenzo[a,d]cycloheptenone by heating with aqueous acid for a period of from 10–50 hours. In a preferred method of carrying out this conversion, a mixture of glacial acetic acid and dilute hydrochloric acid is mixed with the hexafluoro compound and alternately maintained at about 25°C. for a period of 20 hours and heated at 65°C. for about 3 hours. The product is obtained as a residue after concentrating the entire reaction mixture under reduced pressure. The residual crude product is partitioned between water and benzene, sublimed, and chromatographed on a column of silica gel. Selected portions of the eluate from the chromatographic column may be evaporated to produce the desired crystalline tetrafluoro ketone product.

In a still further alternate method of preparing the desired tetrafluoromethyl intermediate, the starting 10,11-dihydro-5H-dibenzo[a,d]cyclohepten-10,11-dione is heated with an excess of sulfur tetrafluoride, mercury, and a small amount of hydrogen fluoride, along with a hydrocarbon solvent, such as methylene chloride or benzene, in an enclosed reaction vessel, for a period of from 5–20 hours, preferably 10 hours, at a temperature of 80°C. The product III produced in this manner is 10,11-dihydro-10,10,11,11-tetrafluoro-5H-dibenzo[a,d]cycloheptene, which is purified in a manner described for the other fluorinated products, i.e., extraction, sublimation, and chromatography on silica gel. The product produced in this manner may be converted to the desired tetrafluoro ketone by oxidation. A preferable method of carrying out the oxidation is to treat a mixture of the 10,11-dihydro-10,10,11,11-tetrafluoro-5H-dibenzo[a,d]cycloheptene and chromium trioxide in trifluoroacetic acid and glacial acetic acid at the refluxing temperature for a period of from 1–5 hours, preferably 2¼ hours. The product is extracted and purified in the manner previously described for the same material 10,11-dihydro-10,10,11,11-tetrafluoro-5H-dibenzo[a,d]cyclohepten-5-one, prepared by the direct fluorination method.

The 10,11-dihydro-10,10,11,11-tetrafluoro-5H-dibenzo[a,d]cycloheptenone intermediate is then converted to the desired 10,11-dihydro-N,N-dimethyl-10,10,11,11-tetrafluoro-5H-dibenzo[a,d]cycloheptene-Δ-5-γ-propylamine by known processes. Thus, the intermediate ketone is reacted with a Grignard reagent formed by the reaction of magnesium and a dialkylaminopropyl halide. The Grignard reagent and the tetrafluoro ketone are mixed while cooling until the reaction is essentially complete, and stirring allowed to continue for a period of approximately 24 hours while maintaining the temperature of about 5°–10°C. Th solvent employed for the reaction is generally one which is inert under the conditions, such as an ether, for example, ethyl ether or tetrahydrofuran. The Grignard addition product is then hydrolyzed under essentially neutral conditions and the bulk of the solvent is removed by evaporation under reduced pressure. The hydrolyzed product is extracted with a solvent, i.e., an aromatic hydrocarbon such as benzene, and the product obtained by evaporation of the solvent under reduced pressure leaving the product, 10,11-dihydro-5-(3-dimethylaminopropyl)-10,10,11,11-tetrafluoro-5H-dibenzo[a,d]cyclohepten-5-ol, as a residual solid.

The thus-obtained product is converted by dehydration using a strong acid under substantially anhydrous conditions; for example, heating at a temperature of from 25°C. to the reflux temperature of a reaction mixture containing the 5-ol compound and a mixture of trifluoroacetic acid and trifluoroacetic anhydride to produce 10,11-dihydro-N,N-dimethyl-10,10,11,11-tetrafluoro-5H-dibenzo[a,d]cycloheptene-Δ-5-γ-propylamine.

EXAMPLE 1

10,11-Dihydro-10,10,11,11-tetrafluoro-5H-dibenzo[a,d]cyclohepten-5-one 10,11-Dihydro-5-H-dibenzo[a,d]cyclohepten-10,11-dione, 0.8 g. (0.0036 mole), together with 75 g. of sulfur tetrafluoride, 1 g. of mercury and a trace of hydrogen fluoride, is charged into a stainless steel autoclave and shaken 2 hours at 120°C., 2 hours at 140°C., and 6 hours at 160°C. After cooling and venting the vessel, the mixture is dissolved in chloroform, separated from mercury, and filtered through diatomaceous earth. Evaporation of solvent from the filtrate under reduced pressure leaves an oily black solid as the residue that is triturated with 75 ml. of boiling hexane. The hexane-insoluble material is removed by filtration and evaporation of solvent from the filtrate under reduced pressure leaves the crude product as an oily black solid. Sublimation at 70°–75°C. and 0.05 mm. yields slightly oily, pale yellow crystals, m.p. 69°–77°C. to a cloudy melt clear at 110°C. Purification is effected by column chromatography on 50 g. of silica gel, the product being eluted with carbon tetrachloride. The fractions that show one spot of Rf 0.2 on a silica thin layer plate developed with carbon tetrachloride are combined. Evaporation of the solvent under reduced pressure leaves white crystals, m.p. 73°–76°C. A sample for analysis is sublimed at 65°C. and 0.05 mm. and recrystallized twice from isopropyl alcohol-water; m.p. 75.5°–77.5°C.

Anal. Calc'd. for $C_{15}H_8F_4O$: C, 64.28; H, 2.88; F, 27.12. Found: C, 64.04; H, 2.88; F, 27.04.

The procedure of the preceding paragraph is repeated utilizing as the starting material the appropriate amount of the substituted 10,11-dihydro-5H-dibenzo[a,d]-cycloheptene-10,11-dione to produce the correspondingly substituted 10,11-dihydro-10,10,11,11-tetrafluoro-5H-dibenzo-[a,d]cyclohepten-5-one, as follows:

| STARTING MATERIAL | PRODUCT |
| --- | --- |
| 10,11-dihydro-1-fluoro-5H-dibenzo[a,d]cycloheptene-10,11-dione | 10,11-dihydro-1,10,10,11,11-pentafluoro-5H-dibenzo[a,d]-cyclohepten-5-one |
| 3-chloro-10,11-dihydro-5H-dibenzo[a,d]cycloheptene-10,11-dione | 3-chloro-10,11-dihydro-10,10,11,11-tetrafluoro-5H-dibenzo[a,d]cyclohepten-5-one |
| 10,11-dihydro-3-methyl-5H-dibenzo[a,d]cycloheptene-10,11-dione | 10,11-dihydro-3-methyl-10,10,11,11-tetrafluoro-5H-dibenzo[a,d]-cyclohepten-5-one |
| 3,7-dimethyl-10,11-dihydro-5H-dibenzo[a,d]cycloheptene-10,11-dione | 3,7-dimethyl-10,11-dihydro-10,10,11,11-tetrafluoro-5H-dibenzo[a,d]cyclohepten-5-one |
| 10,11-dihydro-4-methoxy-5H-dibenzo[a,d]cycloheptene-10,11-dione | 10,11-dihydro-4-methoxy-10,10,11,11-tetrafluoro-5H-dibenzo[a,d]cyclohepten-5-one |
| 10,11-dihydro-3-ethoxy-5H-dibenzo[a,d]cycloheptene-10,11-dione | 10,11-dihydro-3-ethoxy-10,10,11,11-tetrafluoro-5H-dibenzo[a,d]cyclohepten-5-one |
| 3,7-diethoxy-10,11-dihydro-5H-dibenzo[a,d]cycloheptene-10,11-dione | 3,7-diethoxy-10,11-dihydro-10,10,11,11-tetrafluoro-5H-dibenzo[a,d]cyclohepten-5-one |
| 10,11-dihydro-3-trifluoromethyl-5H-dibenzo[a,d]-cycloheptene-10,11-dione | 10,11-dihydro-3-trifluoromethyl-10,10,11,11-tetrafluoro-5H-dibenzo[a,d]cyclohepten-5-one |
| 10,11-dihydro-3-methylmercapto-5H-dibenzo[a,d]-cycloheptene-10,11-dione | 10,11-dihydro-3-methylmercapto-10,10,11,11-tetrafluoro-5H-dibenzo[a,d]cyclohepten-5-one |
| 10,11-dihydro-4-propylmercapto-5H-dibenzo[a,d]-cycloheptene-10,11-dione | 10,11-dihydro-4-propylmercapto-10,10,11,11-tetrafluoro-5H-dibenzo[a,d]cyclohepten-5-one |
| 10,11-dihydro-3-ethylsulfonyl-5H-dibenzo[a,d]-cycloheptene-10,11-dione | 10,11-dihydro-3-ethylsulfonyl-10,10,11,11-tetrafluoro-5H-dibenzo[a,d]cyclohepten-5-one |
| 3-diethylsulfamoyl-10,11-dihydro-5H-dibenzo[a,d]-cycloheptene-10,11-dione | 3-diethylsulfamoyl-10,11-dihydro-10,10,11,11-tetrafluoro-5H-dibenzo[a,d]cyclohepten-5-one |

EXAMPLE 2

10,11-Dihydro-5,5,10,10,11,11-hexafluoro-5H-dibenzo[a,d]cycloheptene 10,11-Dihydro-5H-dibenzo[a,d]cycloheptene-10,11-dione, 1.0 g. (0.0045 mole), together with 48 g. of sulfur tetrafluoride, 1 g. of mercury and a trace of hydrogen fluoride, is charged into a stainless steel autoclave and shaken 10 hours at 80°C. After cooling and venting the vessel, the mixture is dissolved in chloroform, separated from mercury, and filtered. Evaporation of solvent from the filtrate under reduced pressure leaves an oily dark blue residue that is triturated with 150 ml. of boiling hexane. The hexane-insoluble material is removed by filtration and evaporation of solvent from the filtrate under reduced pressure leaving the crude product as the residue. Sublimation at 70°C. and 0.1 mm. yields oily off-white solid that is triturated with carbon tetrachloride. The insoluble material is removed by filtration and the filtrate is concentrated and applied to a chromatographic column of 70 g. of silica gel. The product is eluted with carbon tetrachloride, collecting the fractions that show essentially one spot of Rf 0.7 on a silica thin layer plate developed with carbon tetrachloride. Evaporation of the solvent under reduced pressure and sublimation of the residue at 55°–60°C. and 0.1 mm. yields white crystals, m.p. 53°–55°C. to a slightly cloudy melt.

Anal. Calc'd. for $C_{15}H_8F_6$: C, 59.61; H, 2.67; F, 37.72. Found: C, 59.54; H, 3.11; F, 35.80.

EXAMPLE 3

10,11-Dihydro-10,10,11,11-tetrafluoro-5H-dibenzo[a,d]cyclohepten-5-one

A solution of 989 mg. (0.00328 mole) of 10,11-dihydro-5,5,10,10,11,11-hexafluoro-5H-dibenzo[a,d]cycloheptene in 13.2 ml. of glacial acetic acid - 3.5 ml. of 6 N hydrochloric acid is held at room temperature for approximately 20 hours, heated in a 65°C. bath for 3 hours, again held at room temperature for about 20 hours, and finally heated in a 65°C. bath for 3 hours. The solution is concentrated under reduced pressure and the residue partitioned between benzene and water. The benzene extract is washed with water, dried over anhydrous sodium sulfate, and evaporated to dryness under reduced pressure. Sublimation of the residue at 80°C. and 0.1 mm. yields the crude product as an oily solid. Purification is effected by column chromatography on silica gel, the product being eluted with carbon tetrachloride. The fractions that show one spot of Rf 0.1 on a silica thin layer plate developed with carbon tetrachloride are combined. Evaporation of the solvent under reduced pressure leaves the white crystalline product, m.p. 76°–78°C.

EXAMPLE 4

10,11-Dihydro-10,10,11,11-tetrafluoro-5H-dibenzo[a,d]-cycloheptene 10,11-Dihydro-5H-dibenzo[a,d]cycloheptene-10,11-dione, 2.2 g. (0.01 mole), together with 107 g. of sulfur tetrafluoride, 1 g. of mercury, a trace of hydrogen fluoride, and 25 ml. of methylene chloride, is charged into a stainless steel autoclave and shaken 10 hours at 80°C. After cooling and venting the vessel, the mixture is separated from mercury and filtered. Evaporation of solvent from the filtrate under reduced pressure leaves a brown oil as the residue that is triturated with 150 ml. of hexane. The insoluble tar is removed by filtration and evaporation of solvent from the filtrate under reduced pressure leaves the crude product as an oil. Sublimation at 50°–55°C. and 0.05 mm. yields white crystals, m.p. 53.5°–55°C. A sample for analysis from a previous preparation was purified by column chromatography on silica gel, eluting the product with carbon tetrachloride. Evaporation of solvent under reduced pressure and sublimation of the residual solid at 60°–70°C. and 0.8 mm. gave purified product, m.p. 53.5°–56°C.

Anal. Calc'd. for $C_{15}H_{10}F_4$: C, 67.67; H, 3.79; F, 28.55. Found: C, 67.38; H, 3.89; F, 28.56.

EXAMPLE 5

10,11-Dihydro-10,10,11,11-tetrafluoro-5H-dibenzo[a,d]cyclohepten-5-one

A mixture of 1.45 g. (0.00544 mole) of 10,11-dihydro-10,10,11,11-tetrafluoro-5H-dibenzo[a,d]cycloheptene, 0.73 g. (0.0073 mole) of chromium trioxide, 25 ml. of trifluoroacetic acid and 2 ml. of glacial acetic acid is stirred at reflux for 2¼ hours. During this period, almost all of the chromium trioxide dissolves. Solvents are evaporated under reduced pressure and the residue is partitioned between benzene and water. The aqueous layer is separated and re-extracted twice with benzene. The combined benzene extracts are washed thoroughly with water, dried over anhydrous magnesium sulfate, and evaporated to dryness under reduced pressure. The crude product is left as the residual oily solid and is purified by column chromatography on 75 g. of silica gel, eluting the product with 1:1 benzene-carbon tetrachloride. The fractions that show one spot of Rf 0.75 on a silica thin layer plate developed with benzene are combined. Evaporation of the solvent under reduced pressure leaves the white crystalline product, m.p. 70°–75°C.

EXAMPLE 6

10,11-Dihydro-5-(3-dimethylaminopropyl)-10,10,11,11-tetrafluoro-5H-dibenzo[a,d]cyclohepten-5-ol A solution of 3-dimethylaminopropylmagnesium chloride in 3 ml. of dry peroxide-free tetrahydrofuran is prepared under nitrogen from 0.136 g. (0.0056 g. atom) of magnesium turnings and 0.68 g. (0.0056 mole) of 3-dimethylaminopropyl chloride. To the solution of the Grignard reagent cooled in ice is added dropwise a solution of 0.829 g. (0.00296 mole) of 10,11-dihydro-10,10,11,11-tetrafluoro-5H-dibenzo[a,d]cyclohepten-5-one in 3 ml. of tetrahydrofuran. The mixture is stirred 1 hour in the cold and allowed to stand overnight in the refrigerator. After decanting the solution from any unused magnesium, the bulk of the tetrahydrofuran is evaporated under reduced pressure. The residue is dissolved in benzene, again evaporated under reduced pressure, and the residue redissolved in benzene. The solution is cooled in ice and hydrolyzed by the dropwise addition of 1 ml. of water. The benzene solution is decanted and the residual gelatinous precipitate is re-extracted with benzene. Evaporation of the combined benzene extracts and recrystallization of the residual solid from cyclohexane yields the product, m.p. 155°–157° C. A sample for analysis is recrystallized twice from hexane; m.p. 158°–159°C.

Anal. Calc'd. for $C_{20}H_{21}F_4NO$: C, 65.38; H, 5.76; F, 20.69. Found: C, 65.99; H, 5.38; F, 19.77.

The procedure of the preceding paragraph is repeated using as starting materials the appropriate amount of the substituted 10,11-dihydro-10,10,11,11-tetrafluoro-5H-dibenzo[a,d]-cyclohepten-5-one to produce the correspondingly substituted 10,11-dihydro-5-(3-dimethylaminopropyl)-10,10,11,11-tetrafluoro-5H-dibenzo[a,d]cyclohepten-5-ol, as follows:

| STARTING MATERIAL | PRODUCT |
|---|---|
| 10,11-dihydro-1,10,10,11,11-pentafluoro-5H-dibenzo[a,d]cyclohepten-5-one | 10,11-dihydro-5-(3-dimethylaminopropyl)-1,10,10,11,11-pentafluoro-5H-dibenzo[a,d]cyclohepten-5-ol |
| 3-chloro-10,11-dihydro-10,10,11,11-tetrafluoro-5H-dibenzo[a,d]cyclohepten-5-one | 3-chloro-10,11-dihydro-5-(3-dimethylaminopropyl)-10,10,11,11-tetrafluoro-5H-dibenzo[a,d]cyclohepten-5-ol |
| 10,11-dihydro-3-methyl-10,10,11,11-tetrafluoro-5H-dibenzo[a,d]cyclohepten-5-one | 10,11-dihydro-5-(3-dimethylaminopropyl)-3-methyl-10,10,11,11-tetrafluoro-5H-dibenzo[a,d]cyclohepten-5-ol |
| 3,7-dimethyl-10,11-dihydro-10,10,11,11-tetrafluoro-5H-dibenzo[a,d]cyclohepten-5-one | 3,7-dimethyl-10,11-dihydro-5-(3-dimethylaminopropyl)-10,10,11,11-tetrafluoro-5H-dibenzo[a,d]cyclohepten-5-ol |
| 10,11-dihydro-4-methoxy-10,10,11,11-tetrafluoro-5H-dibenzo[a,d]cyclohepten-5-one | 10,11-dihydro-5-(3-dimethylaminopropyl)-4-methoxy-10,10,11,11-tetrafluoro-5H-dibenzo[a,d]cyclohepten-5-ol |
| 10,11-dihydro-3-ethoxy-10,10,11,11-tetrafluoro-5H-dibenzo[a,d]cyclohepten-5-one | 10,11-dihydro-3-ethoxy-5-(3-dimethylaminopropyl)-10,10,11,11-tetrafluoro-5H-dibenzo[a,d]cyclohepten-5-ol |
| 3,7-diethoxy-10,11-dihydro-10,10,11,11-tetrafluoro-5H-dibenzo[a,d]cyclohepten-5-one | 3,7-diethoxy-10,11-dihydro-5-(3-dimethylaminopropyl)-10,10,11,11-tetrafluoro-5H-dibenzo[a,d]cyclohepten-5-ol |
| 10,11-dihydro-3-trifluoromethyl-10,10,11,11-tetrafluoro-5H-dibenzo[a,d]cyclohepten-5-one | 10,11-dihydro-5-(3-dimethylaminopropyl)-3-trifluoromethyl-10,10,11,11-tetrafluoro-5H-dibenzo[a,d]cyclohepten-5-ol |
| 10,11-dihydro-3-methylmercapto-10,10,11,11-tetrafluoro-5H-dibenzo[a,d]cyclohepten-5-one | 10,11-dihydro-5-(3-dimethylaminopropyl)-3-methylmercapto-10,10,11,11-tetrafluoro-5H-dibenzo[a,d]cyclohepten-5-ol |
| 10,11-dihydro-4-propylmercapto-10,10,11,11-tetrafluoro-5H-dibenzo[a,d]cyclohepten-5-one | 10,11-dihydro-5-(3-dimethylaminopropyl)-4-propylmercapto-10,10,11,11-tetrafluoro-5H-dibenzo[a,d]cyclohepten-5-ol |
| 10,11-dihydro-3-ethylsulfonyl-10,10,11,11-tetrafluoro-5H-dibenzo[a,d]cyclohepten-5-one | 10,11-dihydro-5-(3-dimethylaminopropyl)-3-ethylsulfonyl-10,10,11,11-tetrafluoro-5H-dibenzo[a,d]cyclohepten-5-ol |
| 3-diethylsulfamoyl-10,11-dihydro-10,10,11,11-tetrafluoro-5H-dibenzo[a,d]cyclohepten-5-one | 3-diethylsulfamoyl-10,11-dihydro-5-(3-dimethylaminopropyl)-10,10,11,11-tetrafluoro-5H-dibenzo[a,d]cyclohepten-5-ol |

EXAMPLE 7

10,11Dihydro-N,N-dimethyl-10,10,11,11-tetrafluoro-5H-dibenzo[a,d]cycloheptene-Δ-5-γ-propylamine A solution of 0.58 g. (0.00158 mole) of 10,11-dihydro-5-(3-dimethylaminopropyl)-10,10,11,11-tetrafluoro-5H-dibenzo[a,d]cyclohepten-5-ol in 5 ml. of trifluoroacetic acid - 2.5 ml. of trifluoroacetic anhydride is heated to refluxing for 1½ hours and allowed to stand at 25°C. for 2 hours. Solvents are evaporated under reduced pressure and the residue is partitioned between ether-benzene (60:40) and aqueous sodium hydroxide. After re-extraction of the aqueous phase, the combined organic layers are washed with water, dried over anhydrous sodium sulfate, and evaporated to dryness under reduced pressure. The product is left as the residual oily base and is converted to the hydrogen oxalate salt by treating a solution in isopropyl alcohol with a slight excess of oxalic acid in isopropyl alcohol. The hydrogen oxalate precipitates and is recrystallized from absolute ethanol yielding purified product, m.p. 190°–192°C. Recrystallization from absolute ethanol affords the analytical sample, m.p. 191°–193.5°C.

Anal. Calc'd. for $C_{20}H_{19}F_4N \cdot C_2H_2O_4$: C, 60.13; H, 4.82; N, 3.19, F, 17.29. Found: C, 60.11; H, 4.61; N, 3.08; F, 17.34.

The procedure of the preceding paragraph is repeated using as starting materials, instead of the 10,11-dihydro-5-(3-dimethylaminopropyl)-10,10,11,11-tetrafluoro-5H-dibenzo-[a,d]cyclohepten-5-ol, each of the products obtained in the table from Example 6 with resultant production of the following products:

| STARTING MATERIAL | PRODUCT |
|---|---|
| 10,11-dihydro-5-(3-dimethylaminopropyl)-1,10,10,11,11-pentafluoro-5H-dibenzo[a,d]cyclohepten-5-ol | 10,11-dihydro-N,N-dimethyl-1,10,10,11,11-pentafluoro-5H-dibenzo[a,d]cycloheptene-Δ-5-γ-propylamine |
| 3-chloro-10,11-dihydro-5-(3-dimethylaminopropyl)-10,10,11,11-tetrafluoro-5H-dibenzo-[a,d]cyclohepten-5-ol | 3-chloro-10,11-dihydro-N,N-dimethyl-10,10,11,11-tetrafluoro-5H-dibenzo[a,d]cycloheptene-Δ-5-γ-propylamine |
| 10,11-dihydro-5-(3-dimethylaminopropyl)-3-methyl-10,10,11,11-tetrafluoro-5H-dibenzo-[a,d]cyclohepten-5-ol | 10,11-dihydro-3,N,N-trimethyl-10,10,11,11-tetrafluoro-5H-dibenzo[a,d]cycloheptene-Δ-5-γ-propylamine |
| 3,7-dimethyl-10,11-dihydro-5- | 10,11-dihydro-3,7,N,N-tetra- |

| STARTING MATERIAL | PRODUCT |
|---|---|
| (3-dimethylaminopropyl)-10,10,11,11-tetrafluoro-5H-dibenzo[a,d]cyclohepten-5-ol | methyl-10,10,11,11-tetrafluoro-5H-dibenzo[a,d]cycloheptene-Δ-5-γ-propylamine |
| 10,11-dihydro-5-(3-dimethylaminopropyl)-4-methoxy-10,10,11,11-tetrafluoro-5H-dibenzo[a,d]cyclohepten-5-ol | 10,11-dihydro-N,N-dimethyl-4-methoxy-10,10,11,11-tetrafluoro-5H-dibenzo[a,d]cycloheptene-Δ-5-γ-propylamine |
| 10,11-dihydro-3-ethoxy-5-(3-dimethylaminopropyl)-10,10,11,11-tetrafluoro-5H-dibenzo[a,d]cyclohepten-5-ol | 10,11-dihydro-3-ethoxy-N,N-dimethyl-10,10,11,11-tetrafluoro-5H-dibenzo[a,d]cycloheptene-Δ-5-γ-propylamine |
| 3,7-diethoxy-10,11-dihydro-5-(3-dimethylaminopropyl)-10,10,11,11-tetrafluoro-5H-dibenzo[a,d]cyclohepten-5-ol | 3,7-diethoxy-10,11-dihydro-N,N-dimethyl-10,10,11,11-tetrafluoro-5H-dibenzo[a,d]-cycloheptene-Δ-5-γ-propylamine |
| 10,11-dihydro-5-(3-dimethylaminopropyl)-3-trifluoromethyl-10,10,11,11-tetrafluoro-5H-dibenzo[a,d]cyclohepten-5-ol | 10,11-dihydro-N,N-dimethyl-3-trifluoromethyl-10,10,11,11-tetrafluoro-5H-dibenzo[a,d]-cycloheptene-Δ-5-γ-propylamine |
| 10,11-dihydro-5-(3-dimethylaminopropyl)-3-methylmercapto-10,10,11,11-tetrafluoro-5H-dibenzo[a,d]cyclohepten-5-ol | 10,11-dihydro-N,N-dimethyl-3-methylmercapto-10,10,11,11-tetrafluoro-5H-dibenzo[a,d]-cycloheptene-Δ-5-γ-propylamine |
| 10,11-dihydro-5-(3-dimethylaminopropyl)-4-propylmercapto-10,10,11,11-tetrafluoro-5H-dibenzo[a,d]cyclohepten-5-ol | 10,11-dihydro-N,N-dimethyl-4-propylmercapto-10,10,11,11-tetrafluoro-5H-dibenzo[a,d]-cycloheptene-Δ-5-γ-propylamine |
| 10,11-dihydro-5-(3-dimethylaminopropyl)-3-ethylsulfonyl-10,10,11,11-tetrafluoro-5H-dibenzo[a,d]cyclohepten-5-ol | 10,11-dihydro-3-ethylsulfonyl-N,N-dimethyl-10,10,11,11-tetrafluoro-5H-dibenzo[a,d]-cycloheptene-Δ-5-γ-propylamine |
| 3-diethylsulfamoyl-10,11-dihydro-5-(3-dimethylaminopropyl)-10,10,11,11-tetrafluoro-5H-dibenzo[a,d]-cyclohepten-5-ol | 3-diethylsulfamoyl-10,11-dihydro-N,N-dimethyl-10,10,11,11-tetrafluoro-5H-dibenzo[a,d]cycloheptene-Δ-5-γ-propylamine |

EXAMPLE 8

10,11-Dihydro-10,10,11,11tetrafluoro-5H-dibenzo[a,d]-cyclohepten-5-ol

A solution of 190 mg. (0.005 mole) of sodium borohydride in 1 ml. of water is added dropwise to a stirred solution of 830 mg. (0.00296 mole) of 10,11-dihydro-10,10,11,11-tetrafluoro-5H-dibenzo[a,d]cyclohepten-5-one in 10 ml. of isopropyl alcohol. After stirring the mixture for 3 hours at room temperature and 30 minutes at reflux, the isopropyl alcohol is evaporated under reduced pressure. The residue is partitioned between benzene and water and the benzene extract is separated, washed and dried. Evaporation under reduced pressure leaves the product as the residual pale yellow oil. A sample for analysis is evaporatively distilled at 80°C. and 0.1 mm.

Analysis calc'd. for $C_{15}H_{10}F_4O$: C, 63.84; H, 3.57; F, 26.94. Found: C, 63.93; H, 3.34; F, 26.78.

The procedure of the preceding paragraph is repeated using as the starting material, instead of 10,11-dihydro-10,10,11,11-tetrafluoro-5H-dibenzocyclohepten-5-one, each of the products obtained in accordance with the second paragraph of Example 1 with resultant production of the following products:

10,11dihydro-1,10,10,11,11-pentafluoro-5H-dibenzo[a,d]cyclohepten-5-ol 3-chloro-10,11-dihydro-10,10,11,11-tetrafluoro-5H-dibenzo[a,d]cyclohepten-5-ol 10,11-dihydro-3-methyl-10,10,11,11tetrafluoro-5H-dibenzo[a,d]cyclohepten-5-ol 3,7-diethyl-10,11-dihydro-10,10,11,11-tetrafluoro-5H-dibenzo[a,d]cyclohepten-5-ol 10,11dihydro-4-methoxy-10,10,11,11-tetrafluoro-5H-dibenzo[a,d]cyclohepten-5-ol 10,11-dihydro-3-ethoxy-10,10,11,11-tetrafluoro-5H-dibenzo[a,d]cyclohepten-5-ol 3,7diethoxy-10,11-dihydro-10,10,11,11-tetrafluoro-5H-dibenzo[a,d]cyclohepten-5-ol 10,11-dihydro-3-trifluoromethyl-10,10,11,11-tetrafluoro-5H-dibenzo[a,d]cyclohepten-5-ol 10,11-dihydro-3-methylmercapto-10,10,11,11-tetrafluoro-5H-dibenzo[a,d]cyclohepten-5-ol 10,11-dihydro-3-propylmercapto-10,10,11,11-tetrafluoro-5H-dibenzo[a,d]cyclohepten-5-ol 10,11-dihydro-3-ethylsulfonyl-10,10,11,11-tetrafluoro-5H-dibenzo[a,d]cyclohepten-5-ol 3-diethylsulfamoyl-10,11-dihydro-10,10,11,11-tetrafluoro-5H-dibenzo[a,d]cyclohepten-5-ol

EXAMPLE 9

5-Chloro-10,11-dihydro-10,10,11,11-tetrafluoro-5H-dibenzo[a,d]cycloheptene

A solution of 665 mg. (0.00236 mole) of 10,11-dihydro-10,10,11,11-tetrafluoro-5H-dibenzo[a,d]cyclohepten-5-ol in 5 ml. of dry benzene is stirred, cooled to 10°–15°C. in an ice bath and treated dropwise with 0.2 ml. of thionyl chloride. After allowing the light yellow solution to come to room temperature it is heated to refluxing for approximately 18 hours and the solution is evaporated to dryness under reduced pressure. The residual solid is flushed with benzene three times to remove the last traces of thionyl chloride and finally dried under reduced pressure at 50°C. for 1 hour, yielding product, m.p. 129°–132°C. Recrystallization from petroleum ether (30°–60°C.) affords a purified sample, m.p. 131.5°–133.5°C.

Anal. Calc'd. for $C_{15}H_9ClF_4$: C, 59.91; H, 3.02; Cl, 11.80. Found: C, 60.25; H, 3.26; Cl, 11.63.

The procedure of the preceding paragraph is repeated using as starting materials, instead of 10,11-dihydro-10,10,11,11-tetrafluoro-5H-dibenzo[a,d]cyclohepten-5-ol, each of the products obtained in accordance with the second paragraph of Example 8 with resultant production of 5-chloro-10,11-dihydro-1,10,10,11,11-pentafluoro-5H-dibenzo[a,d]cycloheptene, 3,5-dichloro-10,11-dihydro-10,10,11,11-tetrafluoro-5H-dibenzo[a,d]cycloheptene, 5-chloro-10,11-dihydro-3-methyl-10,10,11,11-tetrafluoro-5H-dibenzo[a,d]cycloheptene, 5-chloro-10,11-dihydro-3,7-dimethyl-10,10,11,11-tetrafluoro-5H-dibenzo[a,d]cycloheptene, 5-chloro-10,11-dihydro-4-methoxy-10,10,11,11-tetrafluoro-5H-dibenzo[a,d]cycloheptene, 5-chloro-10,11-dihydro-3-ethoxy-10,10,11,11-tetrafluoro-5H-dibenzo[a,d]cycloheptene, 5-chloro-3,7diethoxy-10,11-dihydro-10,10,11,11-tetrafluoro-5H-dibenzo[a,d]cycloheptene, 5-chloro-10,11-dihydro-3-trifluoromethyl-10,10,11,11tetrafluoro-5H-dibenzo[a,d]cycloheptene, 5-chloro-10,11-dihydro-3-methylmercapto-10,10,11,11-tetrafluoro-5H-dibenzo[a,d]cycloheptene, 5-chloro-10,11-dihydro-4-propylmercapto-10,10,11,11-tetrafluoro-5H-dibenzo[a,d]cycloheptene, 5-chloro-10,11-dihydro-3-ethylsulfonyl-10,10,11,11-tetrafluoro-5H-dibenzo[a,d]cycloheptene, and 5-chloro-3-diethylsulfamoyl-10,11-dihydro-10,10,11,11-tetrafluoro-5H-dibenzo[a,d]cycloheptene.

EXAMPLE 10

5-(3-Ethoxypropyl)-10,11-Dihydro-10,10,11,11-tetrafluoro-5H-dibenzo[a,d]cycloheptene A Grignard reagent is prepared from 125 mg. of 3-ethoxypropyl bromide and 18 mg. of magnesium in ether. The solution is cooled to room temperature and stirred while a solution of 51 mg. of 5-chloro-10,11-dihydro-10,10,11,11-tetrafluoro-5H-dibenzo[a,d]cycloheptene in 10 ml. of dry tetrahydrofuran is added dropwise with cooling to maintain a temperature of about 25°C. When the addition is complete, the mixture is heated to reflux temperature for about 15 minutes and the bulk of the solvent is then removed by distillation under reduced pressure. The residual material is dissolved in approximately 50 ml. of benzene and 20 ml. of water is added to the mixture. The benzene layer containing the product is washed with water. The benzene extract of the product is evaporated under reduced pressure to yield the product in crude form.

The procedure of the preceding paragraph is repeated using as starting materials, instead of 5-chloro-10,11-dihydro-10,10,11,11-tetrafluoro-5H-dibenzo[a,d]cycloheptene, each of the products obtained in accordance with the second paragraph of Example 9 with resultant production of the following products:

10,11-dihydro-5-(3-ethoxypropyl)-1,10,10,11,11-pentafluoro-5H-dibenzo[a,d]cycloheptene, 3-chloro-5-(3-ethoxypropyl)-10,11-dihydro-10,10,11,11-tetrafluoro-5H-dibenzo[a,d]cycloheptene, 10,11-dihydro-5-(3-ethoxypropyl)-3-methyl-10,10,11,11-tetrafluoro-5H-dibenzo[a,d]cycloheptene, 10,11-dihydro-3,7-dimethyl-5-(3-ethoxypropyl)-10,10,11,11-tetrafluoro-5H-dibenzo[a,d]cycloheptene, 10,11dihydro-5-(3-ethoxypropyl)-4-methoxy-10,10,11,11-tetrafluoro-5H-dibenzo[a,d]cycloheptene, 10,11-dihydro-3-ethoxy-5-(3-ethoxypropyl)-10,10,11,11-tetrafluoro-5H-dibenzo[a,d]cycloheptene, 3,7-diethoxy-10,11-dihydro-5-(3ethoxypropyl)-10,10,11,11-tetrafluoro-5H-dibenzo[a,d]cycloheptene, 10,11-dihydro-5-(3-ethoxypropyl)-3-trifluoromethyl-10,10,11,11-tetrafluoro-5H-dibenzo[a,d]cycloheptene, 10,11-dihydro-5-(3-ethoxypropyl)-3-methylmercapto-10,10,11,11-tetrafluoro-5H-dibenzo[a,d]cycloheptene, 10,11-dihydro-5(3-ethoxypropyl)-5-propylmercapto-10,10,11,11-tetrafluoro-5H-dibenzo[a,d]cycloheptene, 10,11-dihydro-5-(3-ethoxypropyl)-3-ethylsulfonyl-10,10,11,11-tetrafluoro-5H-dibenzo[a,d]cycloheptene, and 3-diethylsulfamoyl-10,11-dihydro-5-(3-ethoxypropyl)-10,10,11,11-tetrafluoro-5H-dibenzo[a,d]cycloheptene.

EXAMPLE 11

5-(3-Bromopropyl)-10,11-dihydro-10,10,11,11-tetrafluoro-5H-dibenzo[a,d]cycloheptene A solution of 1 gram of the product prepared as in Example 10 is dissolved in 5 ml. of a 48% aqueous solution of hydrogen bromide and heated at the reflux temperature for a period of 24 hours with vigorous stirring. The reaction mixture is then cooled and extracted with ether. The ether extract of the product is then washed with water, sodium carbonate solution and with water to neutrality. The ether is removed from the extract by evaporation in vacuo leaving the product, 5-(3-bromopropyl)-10,11-dihydro-10,10,11,11-tetrafluoro-5H-dibenzo[a,d]cycloheptene, as a residual oil.

EXAMPLE 12

10,11-Dihydro-N,N-dimethyl-10,10,11,11-tetrafluoro-5H-dibenzo[a,d]cycloheptene-5-propylamine 1.00 Gram of the product prepared in accordance with the procedure of Example 11 dissolved in 25 ml. of toluene and 5 ml. of dimethylamine is heated to a temperature of 100°C. for a period of 8 hours in a sealed tube. The reaction mixture is then cooled, diluted with ether, and the ethereal solution of the product is washed with water and dried. The ether extract of the product is then evaporated under reduced pressure to produce a residue of 10,11-dihydro-N,N-dimethyl-10,10,11,11-tetrafluoro-5H-dibenzo[a,d]cycloheptene-5-propylamine.

EXAMPLE 13

10,11-Dihydro-N-methyl-10,10,11,11-tetrafluoro-5H-dibenzo[a,d]cycloheptene-5-propylamine 1.00 Gram of the product prepared in accordance with the procedure of Example 11 dissolved in 25 ml. of toluene and 5 ml. of methylamine is heated to a temperature of 100°C. for a period of 8 hours in a sealed tube. The reaction mixture is then cooled, diluted with ether, and the ethereal solution of the product is washed with water and dried. The ether extract of the product is then evaporated under reduced pressure

17 to produce a residue of 10,11-dihydro-N-methyl-10,10,11,11-tetrafluoro-5H-dibenzo[a,d]cycloheptene-5-propylamine.

EXAMPLE 14

10,11-Dihydro-10,10,11,11-tetrafluoro-5H-dibenzo[a,d]cycloheptene-5-propylamine

A mixture of 1 gram of 5-(1-bromopropyl)-10,10,11,11-tetrafluoro-5H-dibenzo[a,d]cycloheptene and 20 ml. of liquid ammonia is heated in a sealed tube at 100°C. for 8 hours. After cooling, the ammonia is allowed to evaporate at room temperature and the residual product diluted with ether and the ethereal solution of the product washed with water, dried, and concentrated to leave as a residue 10,11-dihydro-10,10,11,11-tetrafluoro-5H-dibenzo[a,d]cycloheptene-5-propylamine.

EXAMPLE 15

Secondary Amines Corresponding to Tertiary Amines of Example 7 or 10,11-Dihydro-N-methyl-10,10,11,11-tetrafluoro-5H-dibenzo[a,d]cycloheptene-Δ-5-γ-propylamines Each of the products of Example 7 is converted to the corresponding secondary amine using a known procedure of reaction of each of the products of Example 7 with ethyl chloroformate with intermediate formation of the N-methyl-N-carboethoxy derivative followed by hydrolysis with resultant production of the following products:

10,11-dihydro-N-methyl-10,10,11,11-tetrafluoro-5H-dibenzo[a,d]cycloheptene-Δ-5-γ-propylamine 3-chloro-10,11-dihydro-N-methyl-10,10,11,11-tetrafluoro-5H-dibenzo[a,d]cycloheptene-Δ-5-γ-propylamine 10,11-dihydro-3-N-dimethyl-10,10,11,11-tetrafluoro-5H-dibenzo[a,d]cycloheptene-Δ-5-γ-propylamine 10,11-dihydro-3,7-N-trimethyl-10,10,11,11-tetrafluoro-5H-dibenzo[a,d]cycloheptene-Δ-5-γ-propylamine 10,11-dihydro-4-methoxy-N-methyl-10,10,11,11-tetrafluoro-5-H-dibenzo[a,d]cycloheptene-Δ-5-γ-propylamine 10,11-dihydro-3-ethoxy-N-methyl-10,10,11,11-tetrafluoro-5-H-dibenzo[a,d]cycloheptene-Δ-5-γ-propylamine 3,7-diethoxy-10,11-dihydro-N-methyl-10,10,11,11-tetrafluoro-5H-dibenzo[a,d]cycloheptene-Δ-5-γ-propylamine 10,11-dihydro-N-methyl-3-trifluoromethyl-10,10,11,11-tetrafluoro-5H-dibenzo[a,d]cycloheptene-Δ-5-γ-propylamine 10,11-dihydro-N-methyl-3-methylmercapto-10,10,11,11-tetrafluoro-5-H-dibenzo[a,d]cycloheptene-Δ-5-γ-propylamine 10,11-dihydro-N-methyl-4-propylmercapto-10,10,11,11-tetrafluoro-5H-dibenzo[a,d]cycloheptene-Δ-5-γ-propylamine 10,11-dihydro-3-ethylsulfonyl-N-methyl-10,10,11,11-tetrafluoro-5H-dibenzo[a,d]cycloheptene-Δ-5-γ-propylamine and 3-diethylsulfamoyl-10,11-dihydro-N-methyl-10,10,11,11-tetrafluoro-5H-dibenzo[a,d]cycloheptene-Δ-5-γ-propylamine

What is claimed is:

1. A compound of the formula:

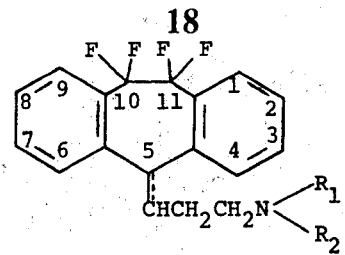

in which
R₁ and R₂ can be alike or different and are either hydrogen, or alkyl of 1–6 carbon atoms, or wherein one to two of the hydrogen atoms attached to the 1-, 3-, 4-, 6-, 7-, or 9- positions is replaced by chlorine, fluorine, alkyl of 1–6 carbon atoms, alkoxy of 1–5 carbon atoms or trifluoromethyl.

2. A compound according to claim 1 of the formula

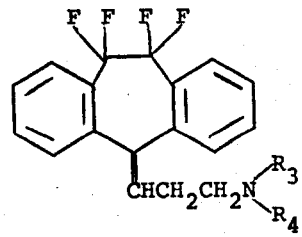

in which R₃ and R₄ are each either hydrogen or loweralkyl of from 1–6 carbon atoms.

3. A compound of the formula

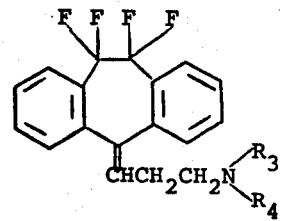

in which R₃ and R₄ are each either hydrogen or loweralkyl of from 1–6 carbon atoms.

4. 10,11-Dihydro-N,N-dimethyl-10,10,11,11-tetrafluoro-5H-dibenzo[a,d]cycloheptene-Δ-5-γ-propylamine.

5. A compound of the formula:

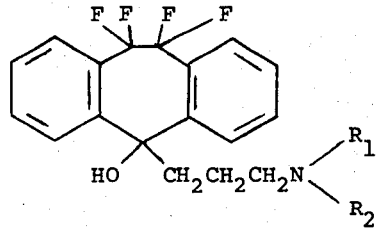

in which
R₁ and R₂ can be alike or different and are either hydrogen, or alkyl of 1–6 carbon atoms, or wherein one to two of the hydrogen atoms attached to the 1-, 3-, 4-, 6-, 7-, or 9- positions is replaced by chlorine, fluorine, alkyl of 1–6 carbon atoms, alkoxy of 1–5 carbon atoms or trifluoromethyl.

6. 10,11-Dihydro-5-(3-dimethylaminopropyl)-10,10,11,11-tetrafluoro-5H-dibenzo[a,d]cyclohepten-5-ol.

7. A compound of the formula:

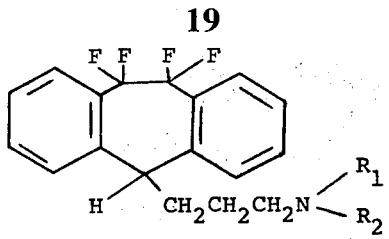

in which
R₁ and R₂ can be alike or different and are either hydrogen, or alkyl of 1–6 carbon atoms, or wherein one to two of the hydrogen atoms attached to the 1-, 3-, 4-, 6-, 7-, or 9- positions is replaced by chlorine, fluorine, alkyl of 1–6 carbon atoms, alkoxy of 1–5 carbon atoms or trifluoromethyl.

8. 10,11-Dihydro-N,N-dimethyl-10,10,11,11-tetrafluoro-5H-dibenzo[a,d]cycloheptene-5-propylamine.

9. 10,11-Dihydro-N-methyl-10,10,11,11-tetrafluoro-5H-dibenzo[a,d]cycloheptene-5-propylamine.

10. 10,11-Dihydro-10,10,11,11-tetrafluoro-5H-dibenzo[a,d]cycloheptene-5-propylamine.

* * * * *